United States Patent [19]

Treille et al.

[11] 4,070,263

[45] Jan. 24, 1978

[54] APPARATUS FOR THE MEASUREMENT OF THE MOBILITY OF COLLOIDS IN AN ELECTRIC FIELD

[75] Inventors: Pierre Albert Eugène Treille, Saint-Cloud; Vincent Dassonville, Charenton; Maurice Gabriel Ernst Bonnemay, Boulogne; Jean Paul Royon, La Varenne-St-Hilaire; Michel Marc Levart, Issy-les-Moulineaux; Henri Pierre Gaessler, Aubervilliers; Yves Robert Richard, Marly-le-Roi, all of France

[73] Assignee: Degremont, Rueil-Malmaison, France

[21] Appl. No.: 722,001

[22] Filed: Sept. 9, 1976

[30] Foreign Application Priority Data

Sept. 16, 1975 France .................................. 75 28334

[51] Int. Cl.$^2$ .................. B01K 5/00; B01D 13/02; G01N 21/06
[52] U.S. Cl. .......................... 204/180 R; 204/299 R; 204/301; 356/105; 356/208
[58] Field of Search .................... 356/105, 208, 246; 324/71 CP; 204/180 P, 180 R, 299, DIG. 11, 301; 250/222 PC

[56] References Cited

U.S. PATENT DOCUMENTS

| | | |
|---|---|---|
| 3,346,478 | 10/1967 | Wiedemann ........................ 356/105 |
| 3,668,107 | 6/1972 | Lappe ................................ 204/180 P |
| 3,849,002 | 11/1974 | Hach .................................. 356/208 |
| 3,865,548 | 2/1975 | Padawer ............................ 356/246 |
| 3,930,736 | 1/1976 | Coulter ............................. 356/246 |
| 3,989,613 | 11/1976 | Gritzner ........................... 204/180 P |

Primary Examiner—Samuel W. Engle
Assistant Examiner—Donald P. Walsh
Attorney, Agent, or Firm—Wenderoth, Lind & Ponack

[57] ABSTRACT

The invention relates to an improved method and apparatus for the measurement of the movement of colloidal particles in suspensions or solutions, wherein an electrophoresis tank is equipped with two electrodes and a filtering membrane positioned substantially parallel and equidistant to the electrodes.

A flat beam of radiation produced at the outside of the tank having a thickness of not more than 1000 $\mu$ as viewed in the direction of the lines of force of the electrical field set up between the electrodes is directed so as to skim the side of the membrane from which the particles move under the effect of the electric field.

With this improved arrangement the influence of secondary interfering phenomena appearing essentially when measuring the movement of colloidal particles in highly mineralized wast waters, can be eliminated.

18 Claims, 2 Drawing Figures

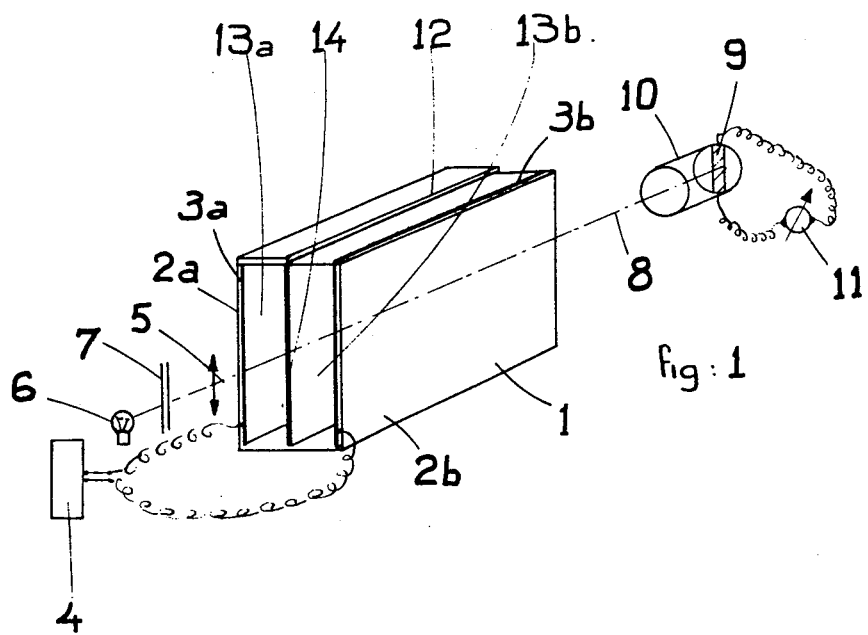
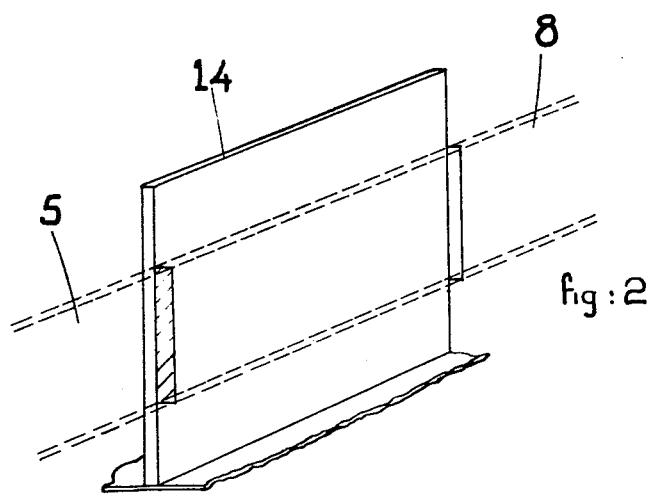

APPARATUS FOR THE MEASUREMENT OF THE MOBILITY OF COLLOIDS IN AN ELECTRIC FIELD

BACKGROUND OF THE INVENTION

There has previously been described in French Patent Application No. 74 30 259, corresponding to U.S. application Ser. No. 605,926 and assigned to the assignee of the present application, a system for measuring the movement of suspended or dissolved colloidal particles which can be used particularly for the treatment of water to determine the optimum dosage of coagulant required for clarification or for regulating the addition of coagulant.

In this known system the movement of the colloids is measured in the immediate neighbourhood of one of the electrodes used for applying an electric field. This electrode is the site of a cathodic transfer reaction allowing the passage of the electrolytic current which is formed between the electrodes, particularly in an aqueous solution. During the passage of the current, that is to say during the measurement, hydrogen is formed and hydroxyl ions are produced. The liberation of gaseous hydrogen and the formation of bubbles which are ordinarily produced at that time are avoided in the known system by use of a platinum cathode which allows the measurement to be made without disturbance.

However, the presence of hydroxyl ions brings about a local pH increase and produces in some instances secondary phenomena having the effect of varying the optical density in the region concerned, that is to say in the region of measurement.

For example, in water super-saturated in bicarbonate there is a rapid precipitation of alkaline earth bicarbonate which clouds the water. In certain highly colloidal waters or in certain coloured waters this alkalisation brings about a noticeable change in the optical density of the solution.

The extent of these interfering phenomena is proportional to the intensity of the measurement current, which is with respect to the water the electrolysis current. This current is itself for a given electrical field proportional to the conductivity of the water. In other words, in the case of a highly mineralised water these phenomena are significant and upset the measurement of optical density in the neighbourhood of the electrode.

It has been observed that in water of resistivity less than 1000 Ω cm, measurement of the variation in optical density in the neighbourhood of the electrode proves impossible.

Furthermore the passage of a significant electrical current in the cell produces, as in every electrophoresis cell, phenomena relating to transport of material wich are liable to upset the measurement.

SUMMARY OF THE INVENTION

The invention has as its objects to relieve these problems and proposes to that effect in an apparatus and method for measuring the mobility of colloidal particles by means of a flat beam of radiation in a continuous electric field, wherein an electrophoresis cell is provided with two substantially parallel electrodes, means for producing the flat beam of radiation, means for energising the electrodes, and a filtering membrane which divides the space between the electrodes into two compartments substantially parallel to the electrodes. The flat beam of radiation passes completely longitudinally through the solution or suspension which is to be measured, at a position closely adjacent the side of the membrane from which the particles are moving under the influence of the electric field. The beam has a thickness of from 0 to 100 $\mu$, preferably from 0 to 500 $\mu$ measured in the direction of the lines of force of the electrical field applied between the electrodes. The compartment which is not crossed by the beam in hermetically sealed during the working of the apparatus.

BRIEF DESCRIPTION OF THE DRAWINGS

In the attached drawings which show schematically and by way of non-limiting example an embodiment of the apparatus of the invention.

FIG. 1 shows the assembly of the devices of which the apparatus is composed; and FIG. 2 shows a partial view of the membrane and the beam of radiation.

DETAILED DESCRIPTION OF THE INVENTION

As has been set out above, the object of the invention is to avoid the disturbance phenomena which are produced in the neighbourhood of the active cathode in the course of measurement carried out on highly mineralised water by means of the apparatus with the previous beam. The solution has been found in spacing the measuring beam from the electrode. However, to retain the advantageous principle there has been placed between the electrodes a filtering membrane allowing passage of the ions present in the solution but not the colloidal particles.

By a process analogus to that of the previous apparatus, the application of an electric field produces downstream of the membrane with respect to the direction of movement of the colloidal particles a reduction in the number thereof proportional to the mobility of these particles.

In this way there is situated a zone in which the measuring beam is transmitted which has a thickness of less than 1000 $\mu$ and preferably less than 500 $\mu$ viewed in the direction of movement of the particles, with the object of detecting in a continuous manner the variation of the number of particles in the zone.

The membrane used according to the invention is a rigid, smooth surface, not exhibiting unevenness greater than 0.2 mm and smooth so as not to be deformed under the action of the pressure which can be produced in the apparatus. In the instances where the material in which the membrane is manufactured is insufficiently rigid it can be held up by means of a support. The material of the membrane is an electrical insulator having a porosity selected so that the ratio between its power of filtration with respect to colloids determined by the size of its pores and its resistance to ionic flux determined by the number of pores which it presents per unit of surface should be optimised.

In practice the membrane will be positioned in such a way that it divides the cup containing the liquid into two compartments of approximately equal volume.

In any event, irrespective of the shape of the cup, the membrane will be placed approximately equi-distant between the two electrodes, where the effect of the disturbances will be felt the least.

In the case of colloids constituted by a suspension of kaolin, for example a membrane having a porosity of 10 $\mu$ is adequate.

It has been found that there can be used with good results: "Millipore Duralon" (trademark of Millipore Co.) membranes having a pore size of 0.2μ; sintered glass No. 2 to 4; various synthetic materials, Dralon 10 μ, polypropylene, etc.

In order to prevent transfer of material by electroosmosis during the measurement, the compartment bounded by the walls of the cell containing the liquid and the membrane, which compartment is not used for the measurement, is hermetically sealed.

The measurements are carried out in a manner analogous to that described in the previous French Application No. 74 30 259, corresponding to U.S. application Ser. No. 605,926, and the same light sources can be used.

The invention will now be described in greater detail with the help of the attached drawings, without the embodiment illustrated therein being considered as a limitation of the invention.

The apparatus consists of parallelepipedal electrophoresis tank or cell 1 whose base is dimensioned 20 mm by 50 mm and whose height is 40 mm. Two electrodes 3a, 3b, each dimensioned 40 × 50 mm and of thickness about 2 mm, are disposed against the lateral walls 2a, 2b. The electrodes are constituted by sheets of palladium. The cell allows a beam length between the walls which are transparent to the radiation of 40 mm. In the middle and parallel to the electrodes is situated a membrane 14 dividing the cell into two compartments 13a and 13b each containing an electrode respectively 3a and 3b.

The membrane has tight joints with the base and the sides of the cell.

A transistor-stabilised supply 4 regulates the intensity of the electrophoresis current. The electrodes are polarised according to the polarity of the colloids by means of a reversing contact (not shown) so that the measurement of mobility can always be carried out in the same compartment 13b.

After filling of the apparatus the compartment 13a is hermetically closed by means of the cover 12 before the measurement proceeds.

An apparatus for measuring the voltage at the terminals of the electrodes allows the electrical field used during the electrophoresis to be determined. The energy is supplied by a 12 volt battery whose capacity is associated with the period of use. The membrane 14 is skimmed by the beam of light 5 from the light source 6 which consists of a 4 watt filament lamp, the beam of light issuing via the intermediate optical system 7 comprising slits of width about 0.5 mm and capable of transforming the diffuse radiation from the light source into uni-directional radiation.

The detection of the luminous intensity of the emergent ray 8 is effected by a photo-resistor cell 9 integrated into a Wheatstone bridge and disposed at the end of a cylindrical tube 10 with opaque walls, or by any other photosensitive cell, the whole assembly constituting the detector cell being disposed opposite the face from which the beam emerges.

The variation in concentration of the colloids in the neighbourhood of the membrane brings about a proportional movement in the needle of the galvanometer 11.

As has been explained above, the apparatus according to the invention is particularly intended for measurement of the optimum dosage of coagulant to be introduced into surface water to bring about its clarification when this water is highly mineralised.

In an identical manner to the practice of the previous apparatus there were prepared as examples four or five samples of water to be clarified. To each sample there is added an increasing quantity of a conventionally used coagulant and the variation in optical density is measured by means of the invention.

That is, a different dosage of coagulant is added to each sample. For each sample there is then taken a first optical density measurement operation before application of the electric field. Thereafter, the electric field is applied, thereby causing unflocculated of the colloidal particles to move in a direction from electrode 3a to electrode 3b. Thereafter, after a predetermined period of time, a second optical density measurement is taken. These first and second optical density measurements are compared to obtain a measurement of the change in optical density of the given sample having a given coagulant dosage therein. After all of the samples are so tested, the measurements of the change in optical density are compared to determine the particular dosage representative of the least amount of change in optical density. This particular dosage represents the optimum dosage to achieve optimum clarification of the liquid to be treated.

The observed fall or change in optical density is reduced at the approach towards the optimum dosage at which maximum flocculation of the colloids will occur. After passing through this "neutral" point the optical density increases on application of the electrical field.

The invention will be described in the following non-limitative examples.

EXAMPLE 1

The optimum dosage of aluminium sulphate to be added to various samples of water to bring about their clarification was determined by means of the previous apparatus (I) described in French Patent Application No. 74 30 259, corresponding to U.S. application Ser. No. 605,926 (without filtering membrane) and then by means of the present invention (II) as described above and including a "Millipore Duralon" (manufactured by Millipore Co.) membrane of a thickness of 0.2 mm.

There were successively added to five samples of a waste water having a restivity of 1800 Ω cm doses of 0, 30, 60, 90 and 120 ppm respectively of aluminum sulphate and measurements in change of optical density were carried out in the two apparatuses (I) and (II) with the cell being subjected to an electric field of 20 V/cm for 3 seconds. The results are given in the table below and are expressed in arbitrary units.

| $Al_2(SO_4)_3$(ppm) | App. (I) | App. (II) |
| --- | --- | --- |
| 0 | −16 | −16 |
| 30 | −12 | −14 |
| 60 | − 8 | − 7 |
| 90 | − 4 | − 4 |
| 120 | + 1 | 0 |

It is observed that with water of this restivity the results ae comparable.

EXAMPLE 2

In a manner identical to that in Example 1 optical density change measurements were carried out by means of the two apparatuses (I) and (II) on white paper from a paper mill having a resistivity of 500 Ω cm.

The doses of coagulant and the results obtained are shown in the following table.

| Al$_2$(SO$_4$)$_3$ ppm | App. I | App. II |
| --- | --- | --- |
| 0 | +6 | −15 |
| 50 | meaningless signal | −10 |
| 100 | " | − 4 |
| 150 | " | − 2 |
| 200 | " | + 2 |

In apparatus (I) where the pH is basic in the vicinity of the electrode, the crude water immediately flocculates and produces a darkening which upsets the measurement. In apparatus (II) according to the invention this phenomenon is not observed.

EXAMPLE 3

In a manner similar to the earlier examples there was measured the quantity of coagulant to be added to clarify waste water from a pharmaceutical laboratory having a resistivity of 100 Ω cm. FeCl$_3$ was used as the coagulant. In apparatus (I) there could not be obtained in this instance a sufficiently high electric field, and no measureable signal was obtained.

The doses of coagulant and the measurement results are given in the table below.

| FeCl$_3$(ppm) | App. I | App. II |
| --- | --- | --- |
| 0 | | −25 |
| 100 | No | −16 |
| 200 | measurable | − 9 |
| 300 | signal | − 2 |
| 350 | | 0 |

We claim:

1. An apparatus for determining the optimum dosage of a coagulant to be added to a liquid to be treated and having colloidal particles suspended therein to achieve optimum clarification of the liquid, said apparatus comprising:
   an electrophoresis cell in the form of a tank having two opposite walls thereof substantially parallelly spaced first and second electrodes;
   a membrane positioned within said tank and extending parallel to said electrodes, said membrane dividing said tank into first and second compartments;
   said tank containing therein, in both said compartments, liquid to be treated, said liquid having added thereto a predetermined dosage of coagulant material to thereby cause flocculation of colloidal particles suspended within said liquid;
   means for passing a flat beam of radiation completely longitudinally through the liquid in said first compartment only at a position closely adjacent said membrane and spaced from said first electrode which is spaced across said first compartment from said membrane, and for maintaining said beam of radiation parallel to said electrodes and to said membrane;
   means for measuring the intensity of said beam of radiation after passage thereof through said first compartment to obtain a measurement of the optical density of the volume of liquid traversed by said beam of radiation;
   means for applying an electric field between said first and second electrodes and for thereby causing unflocculated of said colloidal particles to move in a direction from said second electrode to said first electrode;
   said membrane being formed of a material which is permeable to the passage therethrough of ions in said liquid caused by said electric field but which is impermeable to the passage therethrough of said colloidal particles, whereby during the application of said electric field unflocculated colloidal particles in said second compartment move in a direction from said second electrode toward said membrane but do not pass through said membrane, and unflocculated colloidal particles in said first compartment move in a direction from said membrane toward said first electrode and out of said volume of liquid traversed by said beam of radiation, such that the measurement of optical density as a function of the intensity of said beam of radiation will change as a function of the amount of unflocculated colloidal particles which move out of said volume in said first compartment; and
   said second compartment being hermetically sealed.

2. An apparatus as claimed in claim 1, wherein said beam of radiation has a thickness of from 0 to 1000μ as viewed in the direction of lines of force of said electric field from said second electrode to said first electrode.

3. An apparatus as claimed in claim 2, wherein said thickness is from 0 to 500μ.

4. An apparatus as claimed in claim 1, wherein said beam of radiation is directed through said first compartment at a position to just skim said membrane.

5. An apparatus as claimed in claim 1, wherein said radiation is visible light.

6. An apparatus as claimed in claim 1, wherein said radiation is infra-red radiation.

7. An apparatus as claimed in claim 1, wherein said radiation is gamma radiation.

8. An apparatus as claimed in claim 1, wherein the spacing between said first and second electrodes is from 0.5 to 1.2 cm, and said membrane is positioned midway between said first and second electrodes.

9. An apparatus as claimed in claim 1, wherein the thickness of said membrane is approximately 0.2 mm.

10. A method for determining an optimum dosage of coagulant to be added to a liquid to be treated and having colloidal particles therein to achieve optimum clarification of the liquid, said method comprising:
   providing a tank having at two opposite walls thereof substantially parallelly spaced first and second electrodes and a membrane positioned within said tank and extending parallel to said electrodes, said membrane dividing said tank into first and second compartments;
   performing a plurality of density change measuring operations, each such density change measuring operation comprising:
   placing a quantity of liquid to be treated within said first and second compartments of said tank;
   adding a predetermined dosage of coagulant material to said liquid to thereby cause flocculation of colloidal particles within said liquid;
   passing a flat beam of radiation completely longitudinally through said liquid in said first compartment only at a position closely adjacent said membrane and spaced from said first electrode which is spaced across said first compartment from said membrane, while maintaining said beam of radiation parallel to said electrodes and said membrane;

measuring the intensity of said beam of radiation after passage thereof through said first compartment to obtain a first measurement of optical density of the volume of liquid traversed by said beam of radiation;

thereafter applying an electric field between said first and second electrodes, thereby causing unflocculated of said colloidal particles to move in a direction from said second electrode toward said first electrode;

said membrane being formed of a material which is permeable to the passage therethrough of ions in said liquid caused by said electric field but which is impermeable to the passage therethrough of said colloidal particles, whereby during the application of said electric field unflocculated colloidal particles in said second compartment move in a direction from said second electrode toward said membrane but do not pass through said membrane and unflocculated colloidal particles in said first compartment move in a direction from said membrane toward said first electrode and out of said volume of liquid traversed by said beam of radiation;

thereafter, after a predetermined period of time, again measuring the intensity of said beam of radiation after passage thereof through said first compartment to obtain a second measurement of optical density of said volume of liquid traversed by said beam of radiation, while maintaining said beam of radiation closely adjacent said membrane; and comparing the first and second measurements of optical density to obtain a measurement of the change in optical density of the liquid as a function of the amount of unflocculated of said colloidal particles within said liquid;

the predetermined dosage of coagulant material added in each of said density change measuring operations being different; and comparing the measurements of change in optical density obtained from each of said density change measuring operations to determine the particular dosage representative of the least amount of change in optical density, such particular dosage representing the optimum dosage to achieve optimum clarification of the liquid to be treated.

11. A method as claimed in claim 10, wherein in each of said density change measuring operations said beam of radiation is maintained at a thickness of from 0 to 1000$\mu$ as viewed in the direction of lines of force of said electric field from said second electrode to said first electrode.

12. A method as claimed in claim 11, wherein said thickness is from 0 to 500$\mu$.

13. A method as claimed in claim 10, wherein in each of said density change measuring operations said beam of radiation is directed through said first compartment at a position to just skim said membrane.

14. A method as claimed in claim 10, wherein said radiation is visible light.

15. A method as claimed in claim 10, wherein said radiation is infra-red radiation.

16. A method as claimed in claim 10, wherein said radiation is gamma radiation.

17. A method as claimed in claim 10, wherein the spacing between said first and second electrodes is from 0.5 said first and second electrodes.

18. A method as claimed in claim 10, wherein the thickness of said membrane is approximately 0.2 mm.

* * * * *